US008476387B2

(12) United States Patent
Bergmann et al.

(10) Patent No.: US 8,476,387 B2
(45) Date of Patent: *Jul. 2, 2013

(54) CATALYTIC PROCESS FOR PREPARING (METH)ACRYLIC ESTERS OF N-HYDROXYALKYLATED LACTAMS

(75) Inventors: Hermann Bergmann, Singapore (SG); Frank Hoefer, Bad Duerkheim (DE); Maximilian Angel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 970 days.

This patent is subject to a terminal disclaimer.

(21) Appl. No.: 12/525,826

(22) PCT Filed: Feb. 11, 2008

(86) PCT No.: PCT/EP2008/051584
§ 371 (c)(1),
(2), (4) Date: Aug. 5, 2009

(87) PCT Pub. No.: WO2008/098885
PCT Pub. Date: Aug. 21, 2008

(65) Prior Publication Data
US 2010/0010236 A1 Jan. 14, 2010

(30) Foreign Application Priority Data
Feb. 15, 2007 (EP) .................. 07102481

(51) Int. Cl.
*C08F 26/08* (2006.01)
(52) U.S. Cl.
USPC ........... 526/264; 526/301; 526/310; 526/311; 548/341.5; 560/1
(58) Field of Classification Search
USPC ............. 526/264, 301, 310; 548/341.5; 560/1
See application file for complete search history.

(56) References Cited

U.S. PATENT DOCUMENTS

| 2,882,262 | A | 4/1959 | Smith et al. |
| 3,342,786 | A | 9/1967 | Emmons |
| 3,371,040 | A | 2/1968 | Emmons |
| 7,750,100 | B2 * | 7/2010 | Hoefer et al. ................ 526/264 |
| 8,026,374 | B2 * | 9/2011 | Bergmann et al. ......... 548/341.5 |
| 2003/0113365 | A1 | 6/2003 | Schaberg et al. |
| 2007/0123673 | A1 | 5/2007 | Hofer et al. |

FOREIGN PATENT DOCUMENTS

| DE | 1 595 233 | 10/1969 |
| DE | 2 048 312 | 4/1972 |
| GB | 930 668 | 7/1963 |
| WO | 03 006568 | 1/2003 |
| WO | 2007 051738 | 5/2007 |

OTHER PUBLICATIONS

Iskander, George M. et al., "Synthesis and polymerization of new pyrrolidone-containing methacrylate monomers", Polymer, Elsevier, vol. 39, No. 17, pp. 4165-4169, (Aug. 1, 1998).
U.S. Appl. No. 12/525,686, filed Aug. 4, 2009, Bergmann, et al.
U.S. Appl. No. 12/524,587, filed Jul. 27, 2009, Bergmann, et al.
U.S. Appl. No. 12/597,175, filed Oct. 23, 2009, Brockmeyer, et al.

* cited by examiner

*Primary Examiner* — Susannah Chung
(74) *Attorney, Agent, or Firm* — Oblon, Spivak, McClelland, Maier & Neustadt, L.L.P.

(57) ABSTRACT

Provided is a process for preparing a (meth)acrylic ester (F) of an N-hydroxyalkylated lactam, in which a cyclic N-hydroxyalkylated lactam (L):

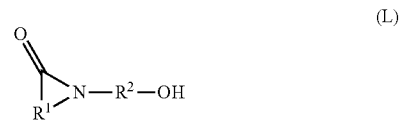

where the structural variables as defined herein, in the presence of at least one metal salt of $C_1$-$C_{10}$-alkoxides (A), is esterified with (meth)acrylic acid (S) or transesterified with at least one (meth)acrylic ester (D), in which the metal salt of $C_1$-$C_{10}$-alkoxides (A) used as a catalyst is added in the absence of solvents and completely at the start of the reaction.

15 Claims, No Drawings

CATALYTIC PROCESS FOR PREPARING (METH)ACRYLIC ESTERS OF N-HYDROXYALKYLATED LACTAMS

The present invention relates to a process for catalytically preparing (meth)acrylic esters of N-hydroxyalkylated lactams and to the use thereof.

In the context of the present invention, (meth)acrylic acid is understood to mean acrylic acid and/or methacrylic acid, and (meth)acrylic esters are understood to mean acrylic esters and/or methacrylic esters. (Meth)acrylic esters are also referred to hereinafter as (meth)acrylates.

(Meth)acrylic esters are prepared usually by catalytically esterifying (meth)acrylic acid or transesterifying other (meth)acrylic esters with alcohols. Strong acids or bases are frequently used, so that acid- or base-sensitive (meth)acrylic esters generally cannot be prepared in a controlled manner by an esterification or transesterification in this way.

(Meth)acrylic esters of N-hydroxyalkylated lactams are known.

WO 03/006568 A1 describes the acidic esterification of acrylic acid with hydroxyethylpyrrolidone using p-toluenesulfonic acid as a catalyst. The yield is, however, only 71%.

German application DE 10 2005 052 931.3, which was yet to be published at the priority date of the present application, discloses a catalytic process for preparing (meth)acrylic esters of N-hydroxyalkylated lactams, in which the esterification or transesterification is performed in the presence of a heterogeneous inorganic salt.

DE 1 595 233 discloses the transesterification of N-hydroxyalkyllactams with (meth)acrylic esters in the presence of titanium tetraalkoxides and alkali metal alkoxides. A disadvantage of this process is that the catalyst has to be removed from the reaction mixture again by an additional purification step, generally a washing step.

GB 930 668 likewise describes the esterification of N-hydroxyalkylatedlactams with (meth)acrylic acid and the transesterification with (meth)acrylic esters. Catalysts which can accordingly be used for the esterification are both acids such as benzenesulfonic acid and titanium tetraalkoxides such as titanium tetraisopropoxide or titanium tetraisobutoxide. For the transesterification, preference is given to using alkaline catalysts such as alkali metal alkoxides or ammonium alkoxides. In addition, the preparation of lactam (meth)acrylates by reacting N-hydroxyalkyllactams with (meth)acryloyl chloride is described. However, the use of (meth)acryloyl chloride in the reactions described leads to salt formation and, owing to its high reactivity, to unselective reactions, for example Michael additions.

A disadvantage of the processes described in the prior art is that the alkali metal alkoxides used as catalysts are used as alcoholic solutions. Furthermore, the catalyst is added gradually in GB 930 668 (example 1) and in DE 1 595 233 (example A), i.e. the catalyst solution is added continuously in the course of the reaction. This is disadvantageous in particular for industrial scale processes.

It was an object of the present invention to provide an alternative process with which (meth)acrylic esters of N-hydroxyalkylated lactams can be prepared in high conversions and high purities from simple reactants. The synthesis should proceed under mild conditions, so that the resulting products have a low color number and high purity. In particular, the process should be performable industrially.

The object is achieved by a process for preparing (meth)acrylic esters (F) of N-hydroxyalkylated lactams, in which cyclic N-hydroxyalkylated lactams (L)

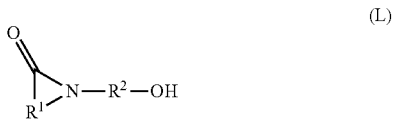

in which $R^1$ is $C_1$-$C_5$-alkylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, with the proviso that $R^1$ must not have any atom other than a carbon atom directly adjacent to the lactam carbonyl group, $R^2$ is $C_1$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, k is from 1 to 50 and $X_i$, for each i=1 to k, may each independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin—O—, —CHVin—$CH_2$—O—, —$CH_2$—CHPh-O— and —CHPh-$CH_2$—O—, in which Ph is phenyl and Vin is vinyl, in the presence of at least one metal salt of $C_1$-$C_{10}$-alkoxides (A), is esterified with (meth)acrylic acid (S) or transesterified with at least one (meth)acrylic ester (D), in which the metal salt of $C_1$-$C_{10}$-alkoxides (A) used as a catalyst is added in the absence of solvents and completely at the start of the reaction.

Hereinafter, the reactants (meth)acrylic acid (S) and (meth)acrylic ester (D) are also summarized together under the term (meth)acrylic compound (B).

With the aid of the process according to the invention, the preparation of (meth)acrylic esters of N-hydroxyalkylated lactams is possible with at least one of the following advantages:

high yield,
mild reaction conditions,
good color numbers and
no washing steps required to purify the reaction mixture.

In the process according to the invention, the metal salt of $C_1$-$C_{10}$-alkoxides (A) used as a catalyst is used in the absence of solvents, i.e. as a pure substance. Preference is given to adding the metal salt of $C_1$-$C_{10}$-alkoxides (A) as a solid. As a result, in contrast to the prior art, no further components, which have to be removed in a complicated manner, are added to the reaction system. This is advantageous especially compared to the prior art, since the methoxides used in the prior art are used in methanolic solutions. Since, however, the transesterification releases methanol, additionally introduced methanol shifts the reaction equilibrium to the side of the reactants.

According to the invention, the metal salt of a $C_1$-$C_{10}$-alkoxide used as the catalyst is added completely at the start of the reaction, i.e. not continuously during the course of the reaction. This is advantageous especially for industrially employable processes, since a gradual or continuous addition of the catalyst is frequently impossible owing to technical problems.

In the above definitions, $C_1$-$C_{20}$-alkylene optionally substituted by aryl, alkyl, aryloxy, alkyloxy, heteroatoms and/or heterocycles is, for example, methylene, 1,2-ethylene, 1,2-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene, $C_5$-$C_{12}$-cycloalkylene optionally substituted by aryl, alkyl, aryloxy, alkyloxy, heteroatoms and/or heterocycles is, for example, cyclopropylene, cyclopentylene, cyclohexylene, cyclooctylene, cyclododecylene, $C_1$-$C_{20}$-alkylene optionally substituted by aryl, alkyl, aryloxy, alkyloxy, heteroatoms and/or heterocycles and interrupted by one or more oxygen and/or sulfur atoms and/or one or more substituted or unsubstituted imino groups and/or by one or more cycloalkyl, —(CO)—, —O(CO)O—, —(NH)(CO)O— —O(CO)(NH)—, —O(CO)— or —(CO)O— groups is, for example, 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylen or 1,4-piperazinylene and $C_6$-$C_{12}$-arylene optionally substituted by aryl, alkyl, aryloxy, alkyloxy, heteroatoms and/or heterocycles is, for example, 1,2-, 1,3- or 1,4-phenylene, 4,4'-biphenylene, tolylene or xylylene.

Examples of $R^2$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene; preference is given to 1,4-butylene, 1,5-pentylene and 1,3-propylene, particular preference to 1,3-propylene.

Examples of $R^2$ are 1,2-ethylene, 1,2-propylene, 1,1-dimethyl-1,2-ethylene, 1-hydroxy-methyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene; preference is given to 1,2-ethylene, 1,2-propylene, 1,3-propylene, particular preference to 1,2-ethylene and 1,2-propylene, and very particular preference to 1,2-ethylene.

Preferred species (L) are N-(2-hydroxyethyl)pyrrolidone, N-(2-hydroxypropyl)pyrrolidone, N-(2'-(2-hydroxyethoxy) ethyl)pyrrolidone, N-(2-hydroxyethyl)caprolactam, N-(2-hydroxypropyl)caprolactam and N-(2'-(2-hydroxyethoxy) ethyl)caprolactam; preference is given to N-(2-hydroxyethyl) pyrrolidone and N-(2-hydroxypropyl)pyrrolidone, particular preference to N-(2-hydroxyethyl)pyrrolidone.

When the N-hydroxylated lactams (L) are optically active, they are preferably used in racemic form or as a diastereomer mixture, but it is also possible to use them as pure enantiomers or diastereomers or as enantiomer mixtures.

In the reaction step, the esterification with (meth)acrylic acid (S) or preferably the transesterification with at least one, preferably exactly one, (meth)acrylic ester (D) is, in accordance with the invention, effected in the presence of at least one metal salt of $C_1$-$C_{10}$-alkoxides (A).

(Meth)acrylic acid (S) may be for the esterification or (meth)acrylic esters (D) of a saturated alcohol may be for the transesterification, preferably saturated $C_1$-$C_{10}$-alkyl esters or $C_3$-$C_{12}$-cycloalkyl esters of (meth)acrylic acid, more preferably saturated $C_1$-$C_4$-alkyl esters of (meth)acrylic acid.

In the context of this document, saturated means compounds without C—C multiple bonds (except of course the C=C double bond in the (meth)acryloyl units).

Examples of compounds (D) are methyl (meth)acrylate, ethyl (meth)acrylate, n-butyl (meth)acrylate, isobutyl (meth) acrylate, tert-butyl (meth)acrylate, n-octyl (meth)acrylate and 2-ethylhexyl (meth)acrylate, 1,2-ethylene glycol di- and mono(meth)acrylate, 1,4-butanediol di- and mono(meth) acrylate, 1,6-hexanediol di- and mono(meth)acrylate, trimethylolpropane tri(meth)acrylate and pentaerythritol tetra (meth)acrylate.

Particular preference is given to methyl (meth)acrylate, ethyl (meth)acrylate, n-butyl (meth)acrylate and 2-ethylhexyl (meth)acrylate, very particular preference to methyl (meth) acrylate, ethyl (meth)acrylate and n-butyl (meth)acrylate, in particular methyl (meth)acrylate and ethyl (meth)acrylate and especially methyl (meth)acrylate.

Metal salts of $C_1$-$C_{10}$-alkoxides (A) usable in accordance with the invention are basic compounds of metal cations and the anion of a $C_1$-$C_{10}$-alcohol. In the context of the present compounds, basic is understood to mean those alkoxides which have a $pK_B$ of not more than 7.0, preferably not more than 6.0 and more preferably not more than 4.0.

The metal cation of the metal salts of $C_1$-$C_{10}$-alkoxides is typically selected from the group consisting of alkali metals and alkaline earth metals, and also aluminum. Preferred alkali metal cations are lithium, sodium and potassium. Preferred alkaline earth metal cations are magnesium and calcium.

Preference is given to using sodium, potassium and aluminum as metal cations of the metal salts of $C_1$-$C_{10}$-alkoxides; very particular preference is given to sodium and potassium.

The anions used are $C_1$-$C_{10}$-alkoxide anions, preferably $C_1$-$C_6$-alkoxide anions. They are, for example, anions of methanol, ethanol, propanol, isopropanol, n-butanol, isobutanol, tert-butanol, n-pentanol and n-hexanol, and isomers thereof. Preferred $C_1$-$C_6$-alkoxide anions are methoxide, ethoxide, n- and isopropoxide and n-, iso- and tert-butoxide; very particular preference is given to methoxide, ethoxide and isopropoxide.

Particularly preferred metal salts of $C_1$-$C_{10}$-alkoxides (A) are sodium methoxide, sodium ethoxide, potassium methoxide and potassium ethoxide.

The esterification or transesterification catalyzed by a metal salt of $C_1$-$C_{10}$-alkoxides (A) is effected generally at from 30 to 140° C., preferably at from 30 to 100° C., more preferably at from 40 to 90° C. and most preferably at from 50 to 80° C.

In a preferred embodiment of the process according to the invention, the reaction is performed under gentle vacuum of, for example, from 200 hPa to standard pressure, preferably from 200 to 600 hPa and more preferably from 300 to 500 hPa when the water released in the esterification or the low-boiling alcohol formed in the transesterification is to be distilled off, if appropriate as an azeotrope.

The molar ratio between (meth)acrylic acid (S) or (meth)acrylic ester (D) and N-hydroxyalkylated lactam (L) is, in the case of the esterification or transesterification catalyzed by a metal salt of $C_1$-$C_{10}$-alkoxides (A), generally 1-6: 1 mol/mol, preferably 1-5: 1 mol/mol and more preferably 1-4: 1 mol/mol.

The reaction time in the esterification or transesterification catalyzed by a metal salt of $C_1$-$C_{10}$-alkoxides (A) is generally from 45 min to 18 hours, preferably from 2 hours to 12 hours and more preferably from 3 to 10 hours.

The content of metal salts of $C_1$-$C_{10}$-alkoxides (A) in the reaction medium is generally in the range from about 0.01 to 5 mol %, preferably 0.1-1.8 mol % and more preferably 0.3-1.5 mol %, based on the sum of the N-hydroxyalkylated lactams (L) used.

In the esterification or transesterification, polymerization inhibitors (as described below) are absolutely necessary.

The presence of oxygenous gases (see below) during the reaction catalyzed by a metal salt of $C_1$-$C_{10}$-alkoxides (A) is preferred.

In the inventive esterification or transesterification, the products are generally obtained with a color number below 500 APHA, preferably below 200 APHA and more preferably below 150 APHA (to DIN ISO 6271).

The reaction can proceed in organic solvents or mixtures thereof or without addition of solvents. The mixtures are generally substantially anhydrous i.e. the water content is below 10% by weight, preferably below 5% by weight, more preferably below 1% by weight and most preferably below 0.5% by weight. Generally the water content is in a range from 100 to 5000 ppm. Moreover, the mixtures are substantially free of primary and secondary alcohols, i.e. alcohol content below 10% by weight, preferably below 5% by weight, more preferably below 1% by weight and most preferably below 0.5% by weight.

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and mono- or polyphasic mixtures thereof.

In a particularly preferred embodiment of the transesterification, the reaction is performed in the (meth)acrylic ester (D) used as the reactant. Very particular preference is given to performing the reaction in such a manner that the product (F), after the reaction has ended, is obtained as an about 10-80% by weight solution in the (meth)acrylic ester (D) used as the reactant, especially as a from 20 to 50% by weight solution.

The reactants are present in dissolved form, suspended as solids or in an emulsion in the reaction medium. According to the invention, the metal salt of $C_1$-$C_{10}$-alkoxides (A) is used in the absence of solvents and preferably as a solid.

The reaction can be effected continuously, for example in a tubular reactor or in a stirred reactor battery, or batchwise. According to the invention, however, the metal salt of $C_1$-$C_{10}$-alkoxides (A) is added completely at the start of the reaction, i.e. not continuously during the course of the reaction.

The reaction can be performed in all reactors suitable for such a reaction. Such reactors are known to those skilled in the art. Preference is given to effecting the reaction in a stirred tank reactor or a fixed bed reactor.

To mix the reaction mixture, any methods may be used. Specific stirrer apparatus is not required. The mixing can be effected, for example, by injecting a gas, preferably an oxygenous gas (see below). The reaction medium may be mono- or polyphasic, and the reactants are dissolved, suspended or emulsified therein. The temperature is adjusted to the desired value during the reaction and can, if desired, be increased or reduced during the course of the reaction.

The removal of water in the case of an esterification, or alcohols which are released from the (meth)acrylic esters (D) in a transesterification, is effected continuously or stepwise in a manner known per se, for example by means of reduced pressure, azeotropic removal, stripping, absorption, pervaporation and diffusion through membranes, or extraction.

The stripping can be effected, for example, by passing an oxygenous gas, preferably air or an air-nitrogen mixture, through the reaction mixture, if appropriate in addition to a distillation.

Suitable media for the absorption are preferably molecular sieves or zeolites (pore size, for example, in the range of about 3-10 angstrom), a removal by distillation or with the aid of suitable semipermeable membranes.

However, it is also possible to feed the mixture of (meth)acrylic esters (D) and its parent alcohol, which frequently forms an azeotrope, directly into a plant for preparing the (meth)acrylic esters (D) in order to reutilize it there in an esterification with (meth)acrylic acid.

After the reaction has ended, the reaction mixture obtained from the esterification or transesterification can be used without further purification or it can, if required, be purified in a further step.

In general, in the workup step, only the catalyst used is removed from the reaction mixture, and the reaction product is removed from any organic solvent used.

A removal from the catalyst is effected generally by filtration, electrofiltration, absorption, centrifugation or decantation, or by distillation or rectification. The catalyst removed can subsequently be used for further reactions.

The removal from the organic solvent is effected generally by distillation, rectification or, in the case of solid reaction products, by filtration.

In the purification step, however, preference is given to removing only the catalyst and any solvent used.

The reaction mixture which has been purified if appropriate is preferably subjected to a distillation in which the (meth)acrylic ester (F) of the N-hydroxyalkylated lactams is separated by distillation from unconverted (meth)acrylic acid (S) or unconverted (meth)acrylic ester (D) and any by-products formed.

The distillation units are usually rectification columns of customary design with a circulation evaporator and condenser. The feed is preferably into the bottom region; the bottom temperature here is, for example, 130-160° C., preferably 150-160° C., the top temperature is preferably 140-145° C. and the top pressure is 3-20 mbar, preferably from 3 to 5 mbar. It will be appreciated that the person skilled in the art can also determine other temperature and pressure ranges in which the particular (meth)acrylic esters (F) of the N-hydroxyalkylated lactams can be purified by distillation. What is essential is a separation of the desired product from reactants and by-products under conditions under which the desired product is exposed to a minimum level of degradation reaction.

The distillation unit has generally from 5 to 50 theoretical plates.

The distillation units are of a design known per se and have the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Barrel or Intalox saddles, Top-Pak, etc., or braids.

Preference is given to distilling the desired product batchwise, which initially removes low boilers from the reaction mixture, usually solvent or unconverted (meth)acrylic acid (S) or (meth)acrylic ester (D). After these low boilers have been removed, the distillation temperature is increased and/or the vacuum is reduced, and the desired product is distilled off.

The remaining distillation residue is usually discarded.

The reaction conditions in the inventive esterification or transesterification are mild. Owing to the low temperatures and otherwise mild conditions, the formation of by-products which can otherwise stem, for example, from strongly acidic or basic catalysts or by undesired free-radical polymerization of the (meth)acrylic compound (B) used, which can otherwise be prevented only by adding stabilizers, in the reaction is prevented.

In the inventive reaction, additional stabilizer may be added to the reaction mixture over and above the storage stabilizer present in the (meth)acrylic compound (B) in any case, for example hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2,2,6,6-tetramethylpiperidine N-oxyl or Uvinul® 4040P from BASF Aktiengesellschaft, or amines such as Kerobit® BPD from BASF Aktiengesellschaft (N,N'-di-sec-butyl-p-phenylenediamine), for example in amounts of from 50 to 2000 ppm.

Advantageously, the esterification or transesterification is performed in the presence of an oxygenous gas, preferably air or air-nitrogen mixtures.

The metal salts of $C_1$-$C_{10}$-alkoxides used in accordance with the invention exhibit merely a low tendency to side reactions. The metal salts are usually sufficiently basic to catalyze an esterification or transesterification but not so basic that they catalyze secondary reactions, for example Michael reactions, to any great extent.

Furthermore, the reaction is very selective under the inventive reaction conditions; generally less than 10%, preferably less than 5%, of by-products are found (based on the conversion).

The (meth)acrylic esters (F) of N-hydroxyalkylated lactams prepared in accordance with the invention find use, for example, as monomers and comonomers in the preparation of dispersions, for example acrylic dispersions, as reactive diluents, for example in radiation-curable coating compositions or in paints, preferably in exterior paints, and also in dispersions for use in the paper sector.

The examples which follow are intended to illustrate the properties of the invention but without restricting it.

EXAMPLES

All "parts" in this document, unless stated otherwise, are understood to mean "parts by weight".

Example 1

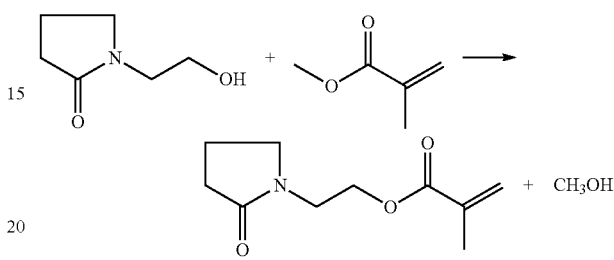

The transesterification was effected in a 750 ml Miniplant reactor with an Oldershaw column and liquid distributor. The reflux ratio was 25:1 (reflux:efflux), the stirrer speed (Anker stirrer) 400 rpm and the air introduction 1.5 l/h.

This apparatus was initially charged with 280 mg of hydroquinone monomethyl ether (350 ppm), 40 mg of phenothiazine (50 ppm), 600 g (6.0 mol) of methyl methacrylate (MMA) and 194 g (1.5 mol) of N-(2-hydroxyethyl)pyrrolidone, which were stirred. Subsequently, 0.81 g (15 mmol; 1.0 mol % based on N-(2-hydroxyethyl)pyrrolidone) of solid sodium methoxide was added, the vacuum was established (300 mbar) and the suspension was heated (the jacket temperature was adjusted to 120° C. by means of thermostating). After approx. 10 minutes, the suspension began to boil; this time was selected as the start point (t=0 min). During the reaction, distillate was removed continuously, and the temperature in the bottom rose from approx. 60° C. to 88° C. and the vapor temperature from approx. 35° C. to 66° C. After 300 min, the reaction was ended and the vacuum was broken. The suspension was cooled and then filtered through a pressure suction filter.

The reaction product was subsequently analyzed by means of GC; it comprised 63.2% product (N-(2-(methacryloyl) ethyl)pyrrolidone), 0.4% N-(2-hydroxyethyl)pyrrolidone and 34.5% methyl methacrylate. The sum of the other by-products was 1.9%.

Subsequently, 200 ppm of Kerobit® BPD (BASF Aktiengesellschaft, N,N'-di-sec-butyl-p-phenylenediamine) were added to the crude product for stabilization. The mixture was distilled under reduced pressure, which first removed excess methyl methacrylate, and then the product of value was obtained (130-131° C. at 1.3 mbar).

266 g (90% yield) of product were obtained with the following composition (GC analysis): 97.5% N-(2-(methacryloyl)ethyl)pyrrolidone, 0.7% N-(2-hydroxyethyl)-pyrrolidone and 1.8% other by-products. Methyl methacrylate was no longer present. The APHA color number was 60.9 g of residue remained in the bottom.

Comparative Example 1

According to GB 930 668, Example 1

Example 1 from GB 930 668 was reworked analogously, except that a mixture of phenothiazine and hydroquinone monomethyl ether was used as the stabilizer instead of p-hydroxydiphenylamine, which is no longer commercially available.

The catalyst solution was prepared by diluting 18 g of a 25% by weight methanolic solution of sodium methoxide with methanol to a volume of 50 ml.

A transesterification apparatus (1 l three-neck flask with mechanical stirrer and distillation system) was initially charged with 285 g (2 mol) of N-(2-hydroxyethyl)-pyrrolidone, 400 g (4 mol) of methyl methacrylate, 2 g of phenothiazine and 2 g of hydroquinone monomethyl ether, which were heated to 90° C. Subsequently, at first 6 g of the catalyst solution was added, and then another 2 g in each case every 5 minutes. Shortly after the first catalyst addition, the mixture began to boil. The mixture was heated until the vapor temperature had risen to >70° C., which was the case after 70 minutes. During the reaction, distillate was removed continuously. Subsequently, the reaction mixture was cooled.

The reaction product was subsequently analyzed by means of GC; it comprised 18.2% product (N-(2-(methacryloyl) ethyl)pyrrolidone), 19.7% N-(2-hydroxyethyl)pyrrolidone and 41.2% methyl methacrylate. The sum of the other by-products was 20.9%.

Subsequently, the crude product was distilled under reduced pressure, which first removed excess methyl methacrylate, and then the product of value was obtained (130-132° C. at 1.5 mbar).

254 g of product were obtained with the following composition (GC analysis): 55.0% N-(2-(methacryloyl)ethyl)pyrrolidone, 43.0% N-(2-hydroxyethyl)pyrrolidone and 2.0% other by-products. Methyl methacrylate was no longer present. The APHA color number was 160. 25.2 g of residue remained in the bottom.

The invention claimed is:

1. A process for preparing a (meth)acrylic ester (F) of an N-hydroxyalkylated lactam, in which a cyclic N-hydroxyalkylated lactam (L)

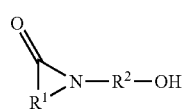

(L)

in which
R$^1$ is C$_1$-C$_5$-alkylene, or C$_2$-C$_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles,
with the proviso that R$^1$ must not have any atom other than a carbon atom directly adjacent to the lactam carbonyl group, and
R$^2$ is C$_1$-C$_{20}$-alkylene, C$_5$-C$_{12}$-cycloalkylene, C$_6$-C$_{12}$-arylene, or C$_2$-C$_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or
R$^2$—OH is a group of the formula —[X$_i$]$_k$—H, in which
k is from 1 to 50 and
X$_i$ for each i=1 to k, may each independently be selected from the group of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin—O—, CHVin-CH$_2$—O—, —CH$_2$—CHPh-O— and —CHPh-CH$_2$—O—, in which Ph is phenyl and Vin is vinyl,
in the presence of at least one metal salt of C$_1$-C$_{10}$-alkoxides (A), is esterified with (meth)acrylic acid (S) or transesterified with at least one (meth)acrylic ester (D), in which the metal salt of C$_1$-C$_{10}$-alkoxides (A) used as a catalyst is added in the absence of solvents and completely at the start of the reaction.

2. The process according to claim 1, wherein the metal salt of C$_1$-C$_{10}$-alkoxides (A) is added as a solid.

3. The process according to claim 1, wherein the metal salt of C$_1$-C$_{10}$-alkoxides (A) has a pK$_B$ of not more than 7.0.

4. The process according to claim 1, wherein the metal salt of C$_1$-C$_{10}$-alkoxides (A) has a metal cation selected from the group consisting of alkali metals, alkaline earth metals and aluminum.

5. The process according to claim 1, wherein the metal salt of C$_1$-C$_{10}$-alkoxides (A) has an alkoxide anion selected from the group consisting of methoxide, ethoxide, n-propoxide, isopropoxide, n-butoxide, isobutoxide and tert-butoxide.

6. The process according to claim 1, wherein the metal salt of C$_1$-C$_{10}$-alkoxides (A) is selected from the group consisting of sodium methoxide, potassium methoxide, sodium ethoxide and potassium ethoxide.

7. The process according to claim 1, wherein R$^1$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene.

8. The process according to claim 1, wherein R$^2$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene.

9. The process according to claim 1, wherein (L) is selected from the group consisting of N-(2-hydroxyethyl)pyrrolidone, N-(2-hydroxypropyl)pyrrolidone, N-(2'-(2-hydroxyethoxy) ethyl)pyrrolidone, N-(2-hydroxyethyl)caprolactam, N-(2-hydroxypropyl)caprolactam and N-(2'-(2-hydroxyethoxy) ethyl)caprolactam.

10. The process according to claim 1, which is performed under a gentle vacuum of from 200 hPa to standard pressure.

11. The process according to claim 1, wherein the metal salt of C$_1$-C$_{10}$-alkoxides (A) is added as a solid.

12. The process according to claim 1, wherein no further components are added to the reaction system.

13. The process according to claim 1, wherein the (meth) acrylic ester (F) is obtained as an about 10-18% by weight solution in the (meth)acrylic ester (D).

14. The process according to claim 1, wherein less than 10% of by-products are formed.

15. The process according to claim 1, wherein less than 5% of by-products are formed.

* * * * *